United States Patent [19]

Silio

[11] 4,242,257
[45] Dec. 30, 1980

[54] PROCESS FOR OBTAINING A NEW GLUCOSE TOLERANCE FACTOR

[76] Inventor: Fernando Silio, Breton de los Herreros, 59 1° D, Madrid, Spain

[21] Appl. No.: 54,535

[22] Filed: Jul. 3, 1979

[30] Foreign Application Priority Data

Jul. 26, 1978 [ES] Spain .................................. 472.034

[51] Int. Cl.$^3$ ..................... C07C 103/52; A61K 37/00
[52] U.S. Cl. ............................... 260/112.5 R; 424/177
[58] Field of Search ................... 260/112.5 R; 424/177

[56] References Cited

PUBLICATIONS

Tuman, R., et al., Chem. Abstr. 89, p. 17663d.
Silio, F., Chem. Abstr. 91, p. 62750g (1979).

*Primary Examiner*—Delbert R. Phillips
*Attorney, Agent, or Firm*—Ladas & Parry

[57] ABSTRACT

A novel glucose tolerance favor is obtained by complexing cobalt and nicotinamide in a ratio 1:2 and reacting the formed complex after acidification with reduced glutathione.

7 Claims, No Drawings

PROCESS FOR OBTAINING A NEW GLUCOSE TOLERANCE FACTOR

The present invention refers to a new glucose tolerance factor and to a process for its preparation.

In rats subjected to a deficient diet containing torula, Schroeder (1957) observed that such diet was deficient in: Vitamin E, selenium and a substance necessary to metabolize glucose (glucose tolerance factor), which would therefore be a co-factor of insulin, but of exogenous origin (diet).

Schroeder himself found, in pigs' kidneys, a substance with biological glucose tolerance factor activity. Subsequently, in co-operation with W. Mertz, he investifated the pesence of said glucose tolerance factor (GTF) in various foods, observing that many foods (very pure carbohydrates) produced a type of obese diabetes, independent from insulin, whereas others (proteins) seemed to provide protection against such diabetes.

W. Mertz subsequently reached the conclusion that one of the components of the GTF was a metal, chromium, and acrried out a series of experiments, including metal chromium (trivalent), which evidenced a discrete increase in the respiration rate (close to 50%) in "in vitro" tests supplemented with GTF extracts or even with relatively high concentrations of trivalent chromium. In test animals, as well as in human beings, the administration of substances rich in GTF or of $Cr^{+++}$ was capable in some cases of correcting the "glucose intolerance" which insulin alone was not capable of doing. It was seen that this type of diabetes due to lack of GTF was an obese or insulin-resistant diabetes where the limiting factor was said GTF.

In 1974 W. Mertz obtained from brewer's yeast a yellowish substance with a GTF activity which was considerably higher than that of metal chromium and, according to the author himself, contained: chromium $3+-$, nicotinic acid and the amino acids glycine, glutanic acid and cysteine.

On reading said publication, I think that the chromium is NOT physiological and, therefore, that its presence in the yeast GTF must come from the stainless steel (18/8) of the fermentation tanks where it is cultured and that, in general, the action of the chromium must be vicarious or substitutive of another biologically active metal, as occurs in many enzymatic systems where magnesium activations can be replaced (partially) with manganese. According to that, what could be the GTF component biologically active metal? In my opinion, it had to be $cobalt^{++}$. Why? Despite the fact that Mertz (1969) indicates that cobalt should not have biological activity, there were data which seemed to confirm the opposite, such as the biological activity of vitamin $B_{12}$ and, with respect to antidiabetic action, I remembered that the medicinal water of Caldas de Malavella contains cobalt. There are quite old references regarding cobalt as a "hipoglucemiating" or antidiabetic substance and the very important observations of Bertand (1926, 1926b, 1927, 1934) on the same subject and the finding of cobalt in the kidney (up to 320 micrograms per kilo of fresh material) which led one to think anew of cobalt as the natural component of the GTF obtained by Schroeder from pigs' kidneys.

As for the rest of the components of the Mertz GTF, I felt that nicotinamide, which is the physiological substance, a component of coenzymes, was much more logical than nicotinic acid.

With respect to the third component (glycine, glutamic acid and cysteine), in nature there is a peptide with that composition (glutathione), a tripeptide having a certain biological activity in which it is possible to include better glucose tolerance in ketotic patients, at a cost of enormous quantities of glutathione.

In actual fact, however, both cobalt and nicotinamide or glutathione, administered alone, are only active as precursors; therefore, they do not produce an immediate action nor do they behave as antidiabetics, even remotely, at the dose at which the GTF may be active.

In case of the GTF, the biological action of said precursors is similar to that of the components of any other coenzyme and the differences thereof with the end product, or biologically active molecule, such as a coenzyme, are as follows: (1) the precursors have to be administered in very high quantities and sufficiently in advance for the entire molecule to synthesize; (2) they are not usually active in "in vitro" biological tests (including enzymatic tests); (3) long term biological activity (there being no immediate activity, as has been said) is very low in relation to the dose administered; (4) when several precursors of the same molecule are administered together their effects may be, in the best of cases, additional, whereas in the case of the end product there is an enormous increase of the effects; (5) on some occasions (as usually occurs with cobalt) one of the precursors alone is absorbed in relatively poor fashion. In fact, in therapeutics many oligoelements are usually administered as organic complexes.

In contrast with these biological properties of precursors, I can specify the properties of a coenzyme or another organic biocatalyst (end product) in the following points: An end product or entire molecule of a coenzyme or organic biocatalyst is characterized in that: (1) It is active at very low concentrations; (2) even in "in vitro" tests and enzymatic tests; (3) action is immediate and its activity is very high in relation to the small dose used; (4) in addition to the increase in the effects of the final molecule there is usually, in many cases, an extremely specific action; (5) the end product usually allows parenteral administration; in many cases it permits the absorption of a component which, as a free element, would not be observed and, via oral administration, at times some biocatalysts may break down into their original components or into intermediate compounds.

A very clear example in this respect can be the biological actions of a coenzyme such as nicotinamide adenine dinucleotide (NAD, DPN or coenzyme 1); in association, its components (adenilic acid, nicotinamide and phosphate) will not be active in enzymatic tests or other "in vitro" tests, whereas "in vivo" quite a number of milligrams will be necessary (being eliminated to a great extent as a methylated derivative in the case of nicotinamide); on the other hand, in the case of the end product, the coenzyme 1 or DPN (or NAD), a fraction of a milligram in injection would be enough to obtain a therapeutic action. The phenomenon is even more marked between DPN and TPN (NAD and NADP), which only differ in one molecule of phosphate but, in general, are selective activators of different enzymatic systems.

The same occurs with flavincoenzyme, FMN and FAD, and even more exaggeratedly with adenosine phosphates: ADP inhibits pyruvate carboxylase and ATP activates it, whereas vice versa ATP inhibits pyruvate dehydrogenase and ADP activates it. The difference only lies in a phosphate incorporated in the molecule.

Synthesis of the Glucose Tolerance Factor

The synthesis is carried out with the three components of my GTF which are:
(a) cobalt$^{2+}$
(b) glutathione
(c) nicotinamide
the synthesis does not take place unless one obtains an intermediate compound, which we can call AC, because it is a cobalt-nicotinamide complex. I have obtained said complex in a state of great purity, perfectly crystallized, and it is totally different from its components A+C. As distinct from the cobalt salts (organic or inorganic) with which I started and which are always of a more or less purplish pink colour, the cobalt nicotinamide complex is of a salmon colour, more or less orange coloured, and perfectly distinguishable from the cobalt salts. Its stoichiometric ratio is: 1 cobalt(ous) for 2 nicotinamide. When this chelate (or intermediate compound, AC) is hydrolized, its components are regenerated and the mauve colour of the cobalt salt appears.

I consider it interesting to point out that: it is not possible to obtain the end product (GTF), that is, the stable brown coloured compound corresponding to the cobalt, nicotinamide, glutathione composition without the previous step of forming the intermediate cobalt nicotinamide compound (AC salmon coloured complex) and that it is not possible to obtain the active end product or cobalt GTF (brown) from the AB (cobalt-glutathione) or BC (nicotinamide glutathione) components, or even from the joint reaction of the three components, A+B+C (cobalt+glutathione+nicotinamide), since I repeat and claim as the process for obtaining the glucose tolerance factor (GTF) of cobalt corresponding to the composition cobalt 1, nicotinamide 2, glutathione 1, the previous step of the intermediate salmon coloured compound which has been referred to as AC and corresponds to the composition: 1 cobaltous for 2 nicotinamide as chelate.

I also wish to claim that: no active product is obtained from cobalt$^3$ (cobaltic), from nicotinic acid or from oxidized glutathione.

The chelate or its salts are obtained with the general method of neutralizing any salt of cobalt$^{2+}$ so that it may thus be displaced by the nicotinamide. It is possible to start, and one actually starts, with different cobalt salts (organic, such as acetate, or inorganic, such as sulfate, chloride, nitrate, etc.), according to price, market availability, etc.); the conditions are not identical, although very similar; as a general rule of the process, one weighs 1 part of cobalt salt which is dissolved in the minimum quantity of water; said solution is neutralized with an alkali which may be concentrated sodium hydroxide at the beginning and diluted ammonia at the end. The nicotinamide is added on neutralizing the cobalt salt, saturating the cobalt with nicotinamide. The optimum proportion is 2 equivalents of nicotinamide for 1 of cobalt in order to observe the stoichiometric ratio of 1:2. The pH is comprised between 5.5 and 7.5, preferably being 6.5.

The different salts of the chelate are obtained from the thus formed chelate, distinguishable by the change in colour from the dark pink of the cobalt salt to a salmon coloured pink of the chelate, by careful acidification (which varies according to the anion one may wish to obtain) up to a pH comprised between 4.5 and 6.5.

One thus obtains orange coloured crystals (of a very different colour from the original colour of the ionic cobalt salt) corresponding to the salt of the 1:2 cobaltous-nicotinamide chelate.

Said compound can then be reacted with a solution of reduced glutathione, in the proportion of 1:1, endeavouring to ensure that the reaction takes place slowly in order to preserve the stability of the chelate. Depending on the form of the chelate, the reaction modifies the pH substantially. At the rate that the reaction takes place, a brown colour corresponding to the end product appears, being completely distinguishable from the orange colour of the chelate. The reaction continues until the clean brown colour becomes permanent and it is then possible to consider the reaction as concluded. From this brown liquid it is possible to obtain the end product in solid form, either by freeze-drying or by precipitation with various volumes (at least 2) of ethyl alcohol.

The end compound, of a brown colour, is reasonably stable, both in solution and in solid form within the range of physiological pH. The product is perfectly soluble in water.

Activity of the Synthetic GTF

My product is biologically active, both in "in vitro" systems, measuring its activity by release of radioactive $CO_2$ produced from 14C glucose incubated with fatty cells of rat epididymis, and in the presence of insulin. It is likewise active for human beings.

The activity of my GTF is proportional to the concentration of insulin, with an optimum concentration, and it is not active in the absence of insulin.

The composition of the product (GTF) obtained by me, by chemical synthesis, is compared with that of the product obtained by W. Mertz from brewer's yeast in the following table.

| Cobalt$^{2+}$+G.T.F. (F. Silio) | Chromium$^{3+}$+G.T.F. (W. Mertz) |
|---|---|
| (1) cobalt$^{2+}$ | (1') chromium$^{3+}$ |
| (2) glutathione | (2') glycine |
|  | cysteine |
|  | glutamic acid |
| (3) nicotinamide | (3') nicotinic acid |

The chromium GTF obtained by Mertz appears to be an artifice, as its action is relatively weak, at very high concentrations, and its biological action is always proportional to the concentration. Its action recalls the hipoglucemiating effects obtained with very high concentrations of: chromium, cobalt, nickel and even inorganic copper, and the mechanism thereof is indirect (enzymatic inhibitions), possibly being a vicarious action of the biologically active product (cobalt).

My GTF (cobalt) is active, "in vitro", at such low concentrations as 4 M$\times 10^{-8}$, the optimum one (for very high insulin concentrations) being slightly higher; at somewhat higher concentrations it inhibits and, as has been said, its action is proportional to the insulin concentration, the GTF being inactive in the absence of said hormone.

The molecular weight of the active compound, calculated by gel-partition (polyacrylamide) shows a molecular weight above 1,500, thus leading one to think that it is not a simple compound with 1 cobalt, 2 nicotinamide, 1 glutathione, but at least 2 molecules or it could even become a tetramer. It is therefore a very complicated structure, but a well defined compound with a very specific biological activity.

I claim:

1. A process for obtaining a glucose tolerance factor, wherein a cobaltous salt in water is neutralized by adding an alkali, nicotinamide is added on neutralization of the cobaltous salt, the formed complex of cobalt and nicotinamide in a ratio of 1:2 is after acidification to a pH of between 4.5 and 6.5 reacted with reduced glutathione and said glucose tolerance factor is obtained.

2. A process according to claim 1 wherein the cobaltous salt used may be an inorganic or an organic salt.

3. A process according to claim 1 wherein the acidification is to a pH of 6.5.

4. A process according to claim 1 wherein the acidification is up to a pH of 6.

5. A process according to claim 1 wherein the complex is formed at a temperature of from about 20° to 80° C., whereas the reaction of the complex with glutathione does not require a special temperature and the pH varies between 4 and 6 depending on the cobaltous salt used.

6. A process according to claim 1 wherein the complex of cobalt and nicotinamide may be used in any of its forms in the reaction with glutathione.

7. A glucose tolerance factor comprising a cobaltous-nicotinamide-glutathione complex obtained by neutralization of a cobaltous salt in water by adding an alkali, addition of nicotinamide on neutralization of the cobaltous salt, acidification to a pH of between 4.5 and 6.5 and reaction of the formed complex of cobalt and nicotinamide in a ratio of 1:2 with reduced glutathione.

* * * * *

UNITED STATES PATENT AND TRADEMARK OFFICE
CERTIFICATE OF CORRECTION

PATENT NO. : 4,242,257
DATED : December 30, 1980
INVENTOR(S) : Fernando Silio

It is certified that error appears in the above-identified patent and that said Letters Patent are hereby corrected as shown below:

In the abstract, line 1, "favor" should read --factor--.

In column 1, line 16, "pesence" should read --presence--.

In column 1, line 23, "acrried" should read --carried--.

In column 1, lines 39 and 40, "glutanic" should read --glutamic--.

Signed and Sealed this

Twenty-first Day of April 1981

[SEAL]

Attest:

RENE D. TEGTMEYER

Attesting Officer     Acting Commissioner of Patents and Trademarks